United States Patent [19]

Rupp et al.

[11] Patent Number: 4,724,206

[45] Date of Patent: Feb. 9, 1988

[54] PROTEIN PRODUCTION USING HYPERTONIC MEDIA

[75] Inventors: Randall G. Rupp, Medfield; Scott Geyer, Allston, both of Mass.

[73] Assignee: Damon Biotech, Inc., Needham Heights, Mass.

[21] Appl. No.: 579,492

[22] Filed: Feb. 13, 1984

[51] Int. Cl.$^4$ .......................... C12P 21/00; C12N 5/00
[52] U.S. Cl. ........................................ 435/68; 435/70; 435/240.22; 435/240.27; 435/240.31
[58] Field of Search ............... 435/178, 240, 241, 278, 435/284, 283, 948, 68, 70, 240.22, 240.27, 240.3, 240.31; 424/85

[56] References Cited

U.S. PATENT DOCUMENTS

| | | | |
|---|---|---|---|
| 3,039,932 | 6/1962 | McLimans et al. | 435/241 |
| 4,138,292 | 2/1979 | Chibata et al. | 195/59 |
| 4,342,833 | 8/1982 | Chirikjian | 435/138 |
| 4,409,331 | 10/1983 | Lim | 435/182 |

FOREIGN PATENT DOCUMENTS 0110384  8/1979  Japan .................................. 435/241

OTHER PUBLICATIONS

P. Brodelius & K. Mosbach, "Immobilized Plant Cells," Advances in Applied Microbiology, vol. 28, pp. 1–26 (1982).
Schachtschabel & Foley, "Serial Cultivation of Erlich Ascites Tumor Cells in Hypertonic Media," Experimental Cell Research, vol. 70, pp. 317–324 (1972).
Stubblefield & Mueller, "Effects of Sodium Chloride Concentration on Growth, Biochemical Composition, and Metabolism of Heha Cells," Cancer Research, vol. 20, Dec. 1960, pp. 1646–1655.
Chemical Abstracts, vol. 82, 1975: 122305s.
Chemical Abstracts, vol. 83, 1975: 94519g.
Chemical Abstracts, vol. 92, 1980: 54962h.
Chemical Abstracts, vol. 97, 1982: 213561y.
Reich et al., Cold Spring Harbor Conferences on Cell Proliferation, vol. 2, pp. 325–331 (1975).
McDonald et al., J. Laboratory Clinical Medicine 85(1), Jan. 1975, pp. 59–66 (1975).
Virology, vol. 8, p. 396 only (1959).

Primary Examiner—Margaret Moskowitz
Attorney, Agent, or Firm—Lahive & Cockfield

[57] ABSTRACT

Disclosed is a method of improving protein production in protein-producing cell cultures. The method comprises the steps of culturing protein-producing cells in a medium comprising essential nutrients, vitamins, salts and amino acids, modified by the addition of increased amounts of amino acids so that the osmolarity of the medium is hypertonic, i.e., above about 340 milliosmoles, preferably within the range of 340 to 450 milliosmoles and most preferably 360 milliosmoles. Cells grown in such media produce protein at levels on the order of four times the protein production in normal, isotonic media.

10 Claims, 5 Drawing Figures

- ○ 250 MILLIOSMOLES
- ● 325 MILLIOSMOLES
- △ 400 MILLIOSMOLES

PROTEIN PRODUCTION USING HYPERTONIC MEDIA

BACKGROUND OF THE INVENTION

This invention relates to a method of improving protein production, particularly antibody production, in animal cell cultures. Briefly, hypertonic rather than isotonic media are used to feed and maintain the cells. This has the effect of increasing cell viability. Such hypertonic media are especially well suited for growing antibody-producing cells such as hybridoma since such cells produce much more antibody without significant modification of their viability or growth rate.

Conventional media for cultivation of mammalian cells are formulated in accordance with Eagle's two seminal papers on the effect of ion concentration on cell growth cycles, see Science, 122: 501-4(1955) and Arch. Biochem. & Biophys., 61;356-66 (1956). Eagle determined that media containing 85-115 mM sodium and 1-10 mM potassium were optimum for growth of both Hela cells and mouse fibroblasts. The formulation of Eagle's basal medium, which forms the basis for almost all animal cell growth media used today, is based on these results.

Eagle's work was followed by Stubblefield and Mueller, see Cancer Res. 20: 1646-1655 (1960), who explored the effects of sodium chloride concentration on growth, biochemical composition, and metabolism of HeLa cells. Stubblefield discovered that higher concentrations of sodium chloride in the growth medium prevented cell replication, leading to a decrease in the number of cells, while promoting RNA and protein synthesis in the cells that survive. Stubblefield theorized that the change in saline content hindered DNA replication thereby preventing mitosis and permitting the cells which survived to grow larger than they otherwise would. The addition of sodium chloride changed the osmolarity of the medium but Stubblefield did not attempt to differentiate between osmotic and ionic effects.

Twelve years later, Schachtschabel and Foley (see Exp. Cell Res. 70: 317-324, 1972) cultured Ehrlich ascites tumor cells in a media made hypertonic by the addition of sodium chloride to determine the effect of high tonicity media on the growth cycle of this type of cells. Schachtschabel found that a salt tolerant population which followed a substantially normal life cycle developed after significant losses in the number of cells in the culture. However, these salt-tolerant cells had a somewhat different morphology than conventional cells, i.e., they appeared more like fibroblast than epithelial cells. The generation or doubling time for these cells increased dramatically and the number of surviving cells decreased as the tonicity of the media was increased.

Antibody-producing cultures, e.g., spleen cells and hybridomas, are normally grown in media such as Eagle's modified media containing serum. Growth cycles for the antibody-producing cells in these media and the amount of antibody secreted is within the expected range as compared with other protein-secreting cells grown in these media. However, the increased use of antibodies as biological tools, particularly through the advances in hybridoma and monoclonal antibody formation techniques, have led to a need for increased antibody production from specific cell cultures.

Myelomas are also grown normally in isotonic media. Since these cells produce protein and can be genetically modified, a medium which could increase protein production level without loss of cell viability would be advantageous.

Accordingly, an object of the invention is to provide a method of culturing protein-producing cells to improve protein production. Another object is to promote high antibody production from antibody-producing cells while developing a viable, expanding culture. A further object is to promote hybridoma growth and monoclonal antibody production without adding feeder cells to the culture. A still further object of the invention is to provide a method of obtaining high protein yield from large volume cultures containing a high density of cells. Another object of the invention is to promote protein production from cells, e.g., myeloma, while retaining cell viability. These and other objects and features of the invention will be apparent from the summary, the drawing, and the description which follow.

SUMMARY OF THE INVENTION

Figure 1:
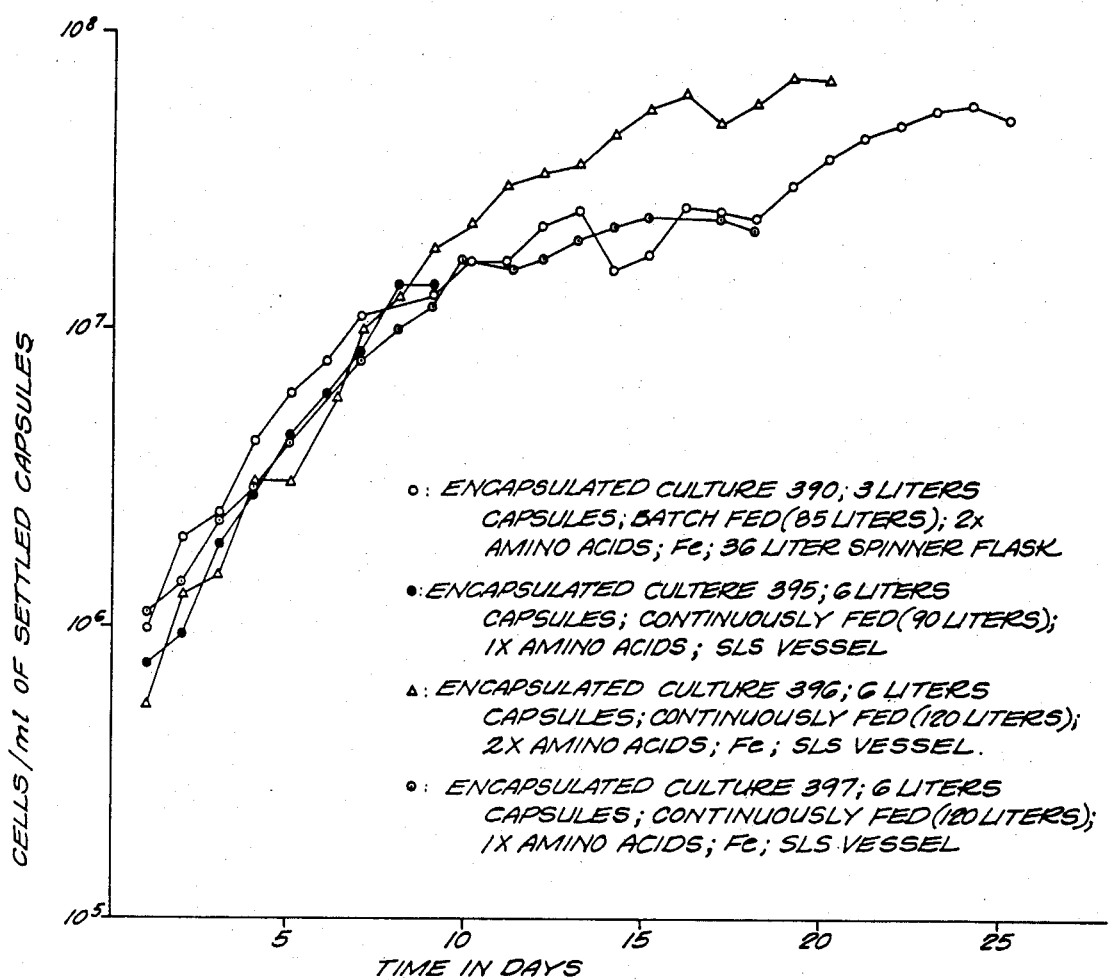
FIG. 1 illustrates the effect on cell population of media made hypertonic by amino acid addition for a culture of antibody producing cells.

The invention features a method of promoting protein production, especially antibody production, in animal cell cultures. In brief, it has been discovered that conventional media used for culturing protein-producing cells can be modified to promote significantly higher protein yields with higher specific activity than has previously been possible. The invention also features an improved growth medium which promotes protein production.

The invention provides a method of promoting protein production by culturing a protein-producing cell in a hypertonic medium, that is, a medium having an osmolarity of at least 340 milliosmoles, preferably having an osmolarity within the range of 340 and 450 milliosmoles, and most preferably about 360 milliosmoles. Preferred media are conventional growth media, e.g., Eagle's media, made hypertonic by the addition of increased amounts of amino acids, preferably twice the normal amino acid content. These amino acids may be added batchwise or on a continuous basis. Conventional medium may be periodically infused with excess amino acids to produce amino acid concentrations greater than those normally employed. Alternatively, a previously prepared hypertonic medium may be continuously or intermittently passed through the culture. Improvement in protein production is also achieved in a batch culture using hypertonic medium. Any protein-producing cell can benefit from the invention, but genetically modified cells are preferred.

While the method of the invention is generally useful for increasing protein production from conventional protein-producing cell cultures, it is particularly useful when the protein-producing cells are encapsulated within a plurality of capsules having a permeable membrane defining an intracapsular volume. The capsule membrane may include a polymer containing a plurality of primary amine groups salt-bonded to an acidic polysaccharide. The preferred acidic polysaccharide is alginate, while the preferred polymer containing a plurality of primary amine groups is a polypeptide, most preferably polylysine or polyornithine.

The invention includes an improved growth medium for promoting protein production. This medium contains essential salts, nutrients and amino acids necessary for cell growth and mitosis, as do media such as Eagle's modified media, but are modified by the addition of excess amino acids sufficient to increase the osmolarity of the medium to at least about 340 miliosmoles, preferably between about 340 and 450 milliosmoles, and most preferably about 360 milliosmoles. Media embodying the invention promote increased protein production without affecting adversely viability of the cells or their growth rate.

DESCRIPTION

The method and medium of the invention are based on the discovery that, in contrast to conventional belief, hypertonic media can promote protein, particularly antibody, production without damaging the viability of the cells. Exceptional antibody yields, having higher specific activity or purity than had previously been possible, are obtained following the teaching of the invention, in either small volume cultures or large, high cell density, production sized cultures.

Early experiments on the effect of sodium chloride concentration on HeLa and mouse fibroblast cells led to the conclusion that 290 to 330 milliosmoles was the optimum tonicity range for growth of animal cell culture. However, if one uses the method of the invention, one can achieve antibody yields of 50% of secreted protein, and yields of up to 62% are possible. Because of the high antibody concentration in the secreted protein, purification of the antibody is facilitated, thereby alleviating many of the problems associated with antibody purification and reducing the cost of such purification. Hypertonic media are particularly useful for culturing hybridomas, myelomas, and other continuous mammalian cell protein-producing cultures, yielding higher protein production or secretion levels than is possible with conventional media. Myelomas can be genetically modified to promote production of specific proteins.

Protein-producing cells for use in the invention may be grown in large cultures having cell densities on the order of $10^8$ cells/ml in accordance with the procedures disclosed in U.S. Pat. No: 4,352,883, U.S. Pat. No. 4,409,331, and copending application Ser. No. 579,493 filed on even date herewith, the disclosures of which are incorporated herein by reference. Briefly, the U.S. Pat. Nos. 4,352,583 and 4,409,331 disclose methods of encapsulating healthy, viable cells and methods of harvesting substances produced by the cells. Ser. No. 579,493 discloses that extraordinarily high cell densities may be achieved in encapsulated cultures using conventional media if the oxygen and carbon dioxide requirements are met by sparging a gas of defined oxygen and carbon dioxide content directly through an encapsulated culture. Employing these techniques, cultures having a volume on the order of 30 liters and a cell density of $10^8$ cells/ml have been produced. Using the process of this invention, such cultures have produced on the order of 3-6 grams of monoclonal antibody.

Figure 5:
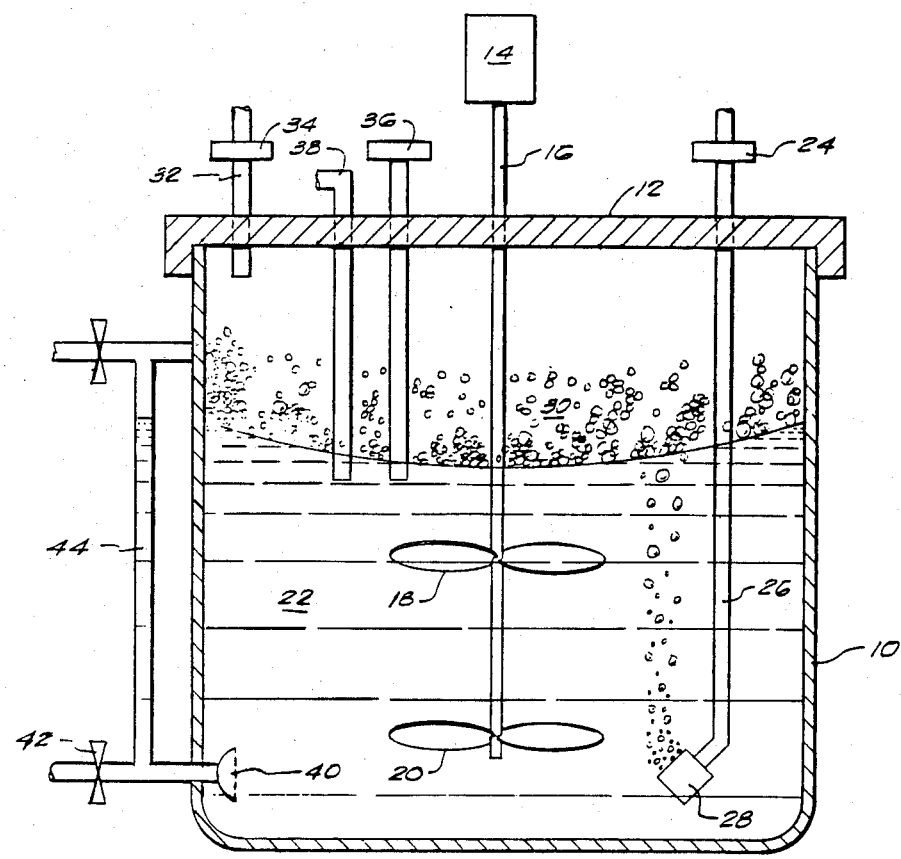
FIG. 5 illustrates apparatus useful in producing protein in accordance with the invention.

FIG. 5 schematically illustrates apparatus for culturing cells in accordance with the invention. It comprises a 316L stainless steel, electropolished, 50 liter capacity vessel 10 fitted with a headplate 12. A motor 14 drives paddle shaft 16 to rotate paddles 18 and 20 disposed within the culture 22. Culture 22 comprises the hypertonic medium, e.g., as defined hereinafter, and a multiplicity of suspended capsules having mombranes permeable to the amino acids, gases, vitamins, ions, etc., contained in the medium. The currently preferred hypertonic medium is modified Eagle's medium containing twice the normal concentration of amino acids and supplemented with 5% by volume serum, e.g., bovine serum. Typically, the capsules are spherical or spheroidal and have a diameter on the order of less than about 2 mm. Capsules having an average diameter on the order 0.8 mm work well. The gas requirements of the cells are met by passing an oxygen and carbon dioxide-containing gas through sterile filter 24, air tube 26, and sparging head 28. Sparging head 28 may comprise a 2.5 micron porous porcelin filter. The gas may comprise 95% air 5% $CO_2$ (by volume). Gas bubbles pass from the sparging head 28 up through the medium among the capsules. The rate of sparging should be sufficient to maintain the partial pressure of oxygen in the medium substantially equal to the partial pressure of oxygen in the gas. The pressure of oxygen in the medium may thereby be set to a level at or slightly above that which the cells require for optimal growth. Because of the serum components in the medium, sparging causes foam to collect in the headspace 30 of vessel 10. However, the capsules protect the cells from dehydration should they temporarily be transported into the foam, and also protect the cells from mechanical damage. Thus, gas sparging through an encapsulated culture can satisfy the need of the increasing cell population for oxygen, thereby enabling extremely high cell densities to be achieved. Gas exiting the culture passes through exit port 32 and filter 34. A typical gas flow rate for a 30 liter culture is 0.2 standard cubic feet per hour.

When practicing the invention in the batch-feeding mode, the hypertonic medium is simply metered into vessel 10 together with microcapsules containing the seed culture, and the culture is grown to maximum density. Alternatively, an isotonic, conventional medium may be employed at the outset, and additional, one or more times during the growth cycle, e.g., through injection port 36. However, perhaps the best way of practicing the invention is to pass hypertonic medium through the culture by introducing a continuous or intermittant flow of medium into entry port 38, and draining off medium through filter element 40. Filter element 40 may comprise a stainless, microporous mesh having pores smaller than the diameter of the capsules, e.g., 50 to 100 microns. Medium may be withdrawn through valve 42. The level of medium in the culture may be observed in transparent site tube 44. A typical rate of medium flow into entry port 38 and out through filter 40 is 4 ml to 12 ml per minute. It is also contemplated that an enriching amino acid solution may be injected into the culture as required to maintain a desired hypertonicity.

The method employed in harvesting protein produced by the cells will depend upon the relationship of the effective molecular dimensions of the protein of interest and the permeability of the capsule memberanes. As disclosed in the above-referenced patents, the permeability of the capsule membranes can be controlled within limits. Details of the currently preferred method of controlling capsule membrane porosity and making uniform capsules are disclosed in pending application Ser. No. 579,494, the disclosure of which is incorporated herein by reference. If the protein of interest is too large to traverse the membrane, the protein collects within the microcapsules; if it is small enough to traverse the membranes, it will collect in the extracapsular medium.

The following nonlimiting examples will further illustrate the invention.

EXAMPLE 1

This experiment illustrates that increasing the tonicity of the culture medium by the addition of excess amino acids does not alter the viability of rate of cell mitosis of protein producing cells but does cause increased protein production. The cells used in this experiment were a mouse-mouse hybridoma secreting IgG. The hybridomas were encapsulated by a modification of the procedure set forth in the U.S. Pat. No. 4,352,883. More particularly, a suspension containing about $10^6$ cells/ml in 1% (w/v) sodium alignate (NaG-Kelco LV) in standard medium was transferred to a jet-head apparatus consisting of a housing having an upper air intake nozzle and an elongate hollow body friction fitted into a stopper. The cell density of the alginate-medium suspension dictates the average number of cells per capsule in the seed culture. A syringe, e.g., a 10 cc syringe, equipped with a stepping pump was mounted atop the housing with a needle, e.g., a 0.01 inch I.D. Teflon-coated needle, passing through the length of the housing. The interior of the housing was designed such that the top of the needle is subjected to a constant laminar airflow which acts as an air knife. In use, the syringe full of the solution containing the material to be encapsulated is mounted atop the housing, and the stepping pump is activated to incrementally force drops of the solution to the tip of the needle. Each drop is "cut off" by the air stream and falls approximately 2.5-3.5 cm into a 1.2% (w/v) calcium chloride solution, forming gelled masses which are collected by aspiration. The gelled masses may be incubated in three replenished volumes of isotonic saline for gel expansion. In total, the saline expansion takes approximately 11 minutes. Next, a membrane is formed about the gelled masses by contact with a 750 mg/l poly-L-lysine (Sigma Chemical Company, 65,000 dalton molecular weight) in isotonic saline solution. After 12 minutes of reaction, the resulting capsules are washed for 10 minutes with 1.4 g/l solution of CHES (2-cycloheylamino ethane sulfanic acid) buffer (Sigma) containing 0.2% (w/v) calcium chloride in saline. The capsules are washed for approximately 8 minutes with 0.3% (w/v) calcium chloride in saline, and a second membrane is formed about the capsules by a 10 minute reaction with 105 mg/l polyvinyl amine (Polyscience, 50,000-150,000 dalton molecular weight) in saline. The capsules were washed again with two volumes of isotonic saline over 7 minutes and post-coated with a 7 minute immersion in $5 \times 10^{-2}$% (w/v) NaG solution in saline. The capsules were washed for an additional 4 minutes in saline, then the intracapsular volumes were reliquified by two immersions in 55 mM sodium citrate in saline solution, the first for 20 minutes and the second for 6 minutes. The capsules were washed twice in saline and once for 4 minutes in medium. As disclosed generally in U.S. Pat. No. 4,409,331, when the capsules are incubated in the growth medium IgG collects within the capsules with only trace quantities detectable in the extracapsular medium. Capsules prepared according to this procedure are substantially impermeable to IgG but permit free transverse of required nutrients thereby permitting cell growth and antibody production within the intracapsular volume.

Table 1 lists the ingredients of a basic, known culture medium while Tables 2 and 3 specify the amino acid and vitamin constituents of this medium. The concentrations in parenthesis in Table 1 represent the modifications made in the iron and amino acid content to form a hypertonic medium of the invention. Briefly, the iron was increased by a factor of 100 and the amino acid content was doubled. After formulating the medium, 5% by volume fetal bovine serum is added. The addition of the excess amino acids and ferric nitrate increases the osmolarity of the medium to about 360 milliosmoles. As will be apparent from a review of the constituents of the medium, approximately 4.7% by weight (not including water) comprises amino acid in the normal medium, whereas the hypertonic medium contains approximately 8.9% amino acids. The preferred media of the invention comprise between about 7.0% and 12% amino acids.

TABLE 1

Prepared in 40 liter lots

| Chemical Component | Amount Used |
| --- | --- |
| D (+) Glucose | 80.0 g |
| NaCl | 274.4 g |
| Na$_2$HPO$_4$ (anhydrous) | 4.96 g |
| KCl | 16.0 g |
| MgSO$_4$ (anhydrous) | 3.92 g |
| NaHCO$_3$ | 88.0 g |
| Stock Solutions | |
| ZnSO$_4$.7H$_2$O conc: $10^{-6}$ g/ml | 8.0 ml |
| CuSO$_4$.5H$_2$O conc: $10^{-5}$ g/ml | 0.4 ml |
| Fe(NO$_3$)$_3$.9H$_2$O conc: $10^{-6}$ g/ml ($10^{-4}$ g/ml) | 4.0 ml |
| MnCl$_2$.4H$_2$O conc: $10^{-5}$ g/ml | 0.4 ml |
| Amino Acids conc: 50X | 800 ml (1600 ml) |
| Vitamins conc: 50X | 800 ml |
| PIPES | 136.96 g |
| L-Tyrosine | 1.40 g |
| L-Cystine | 0.80 g |
| CaCl$_2$ | 5.88 g |
| Phenol Red | 0.4 g |

Q.S. to 40 liters with distilled water.

TABLE 2

Prepared in 20 liter lots

| Amino Acid | Amount Used |
| --- | --- |
| L-alanine | 90.0 g |
| L-arginine HCl | 60.0 g |
| L-aspartic acid | 24.0 g |
| L-asparagine H$_2$O | 20.0 g |
| L-cysteine HCl.H$_2$O | 60.0 g |
| L-glutamic acid | 45.0 g |
| Glycine | 50.0 g |
| L-histidine HCl.H$_2$O | 20.0 g |
| L-isoleucine | 30.0 g |
| L-leucine | 75.0 g |
| L-lysine HCl | 90.0 g |
| L-methionine | 23.0 g |
| L-phenylalanine | 25.0 g |
| L-proline | 30.0 g |
| L-serine | 10.0 g |

TABLE 2-continued

Prepared in 20 liter lots

| Amino Acid | Amount Used |
| --- | --- |
| L-threonine | 40.0 g |
| L-tryptophan | 10.0 g |
| L-valine | 50.0 g |

Q.S. to 20 liters with distilled water

TABLE 3

Prepared in 10 liter lots

| VITAMIN | Amount Used |
| --- | --- |
| Ascorbic Acid | 1.0 g |
| d-Biotin | 0.3 g |
| d-Calcium pantothenate | 0.5 g |
| Choline chloride | 0.8 g |
| d-Alpha tocopherol acetate | 6 µl |
| Ergocalciferol | 0.5 g |
| Glutathione | 0.55 g |
| Myo-Inositol | 1.0 g |
| Menadione Sodium Bisulfite | 0.046 g |
| Methyl linoleate | 17 µl |
| Nicotinamide | 0.5 g |
| Pyridoxal-HCl | 0.5 g |
| Riboflavin | 0.05 g |
| Sodium Pyruvate | 12.5 g |
| Thiamine HCl | 0.52 g |
| Vitamin A | 0.05 g |
| Vitamin B12 | 0.1 g |

Q.S. to 10 liters with distilled water

The encapsulated hybridomas were split into four cultures designated 390, 395, 396, and 397. Culture 390, consisting of 6 liters of medium (comprising about 3 liters of settled capsules), was cultured in a 36 liter spinner flask. The initial culture medium was the hypertonic medium containing twice the amino acid content and excess iron. This culture was batchfed six to eight liters of hypertonic culture medium at days 3, 5, 7, 10, 11, 12, 16, 17, 18, 19, 20, and 21 to maintain the tonicity.

Culture 395, containing 6 liters of encapsulated culture in a stainless steel vessel, was continuously fed a total of 90 liters of normal medium over the 26 day period of the experiment. The amino acid concentration (800 ml) employed resulted in an isotonic medium.

Cultures 396 and 397, each containing 6 liters of encapsulated culture in a stainless steel vessel, were continuously fed 120 liters of medium and additional iron over the 26 day period. Culture 396 received the hypertonic medium with twice the amino acids while Culture 397 received isotonic medium. Oxygen/$Co_2$ was sparged through all encapsulated culture.

FIG. 1 illustrates the number of cells/ml of settled capsules at various times for the four cultures. The cell counts were made using a hematocytometer after disrupting a sample of the capsules. As is evident, the hypertonic medium not only did not hinder hybridoma growth, it may actually have increased the growth rate, an entirely unexpected result.

Figure 2:
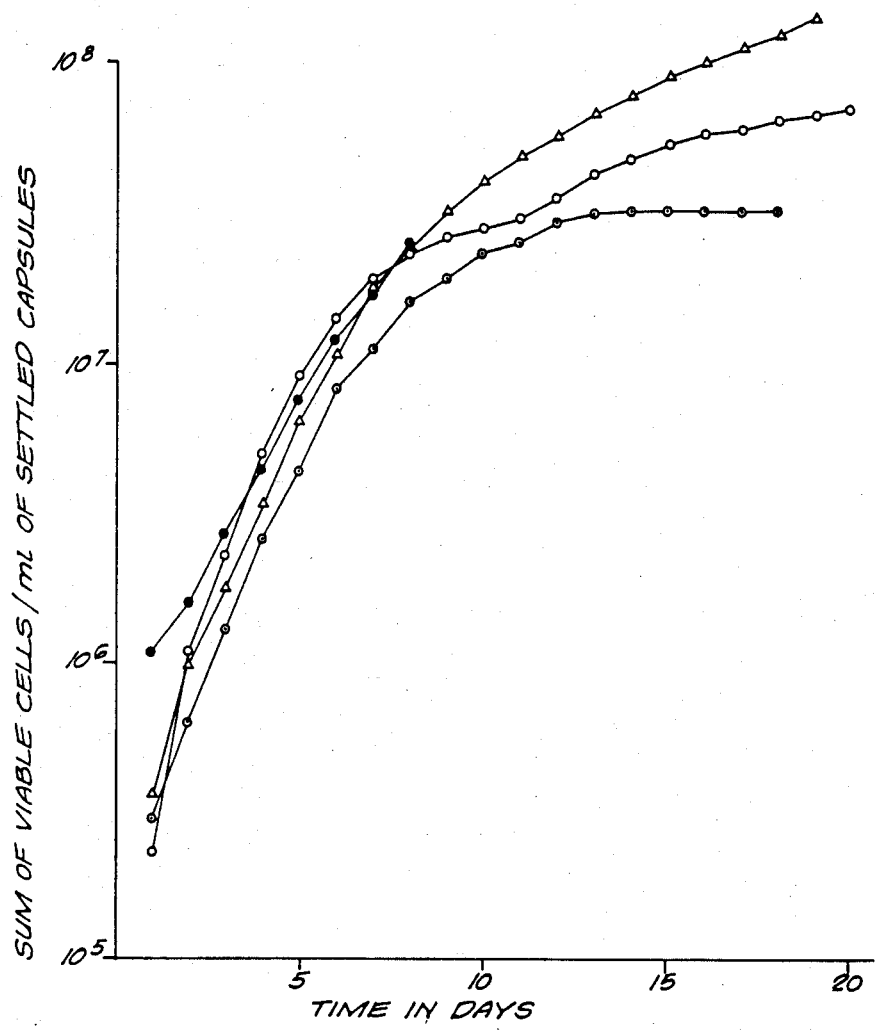
FIG. 2 illustrates the viability of cells grown in the media of FIG. 1.

FIG. 2 illustrates the sum of the viable cessl/ml of settled capsules for the cultures of FIG. 1. The viability of the cells in the hypertonic medium is at least as good, if not better, than it is in isotonic medium.

Figure 3:
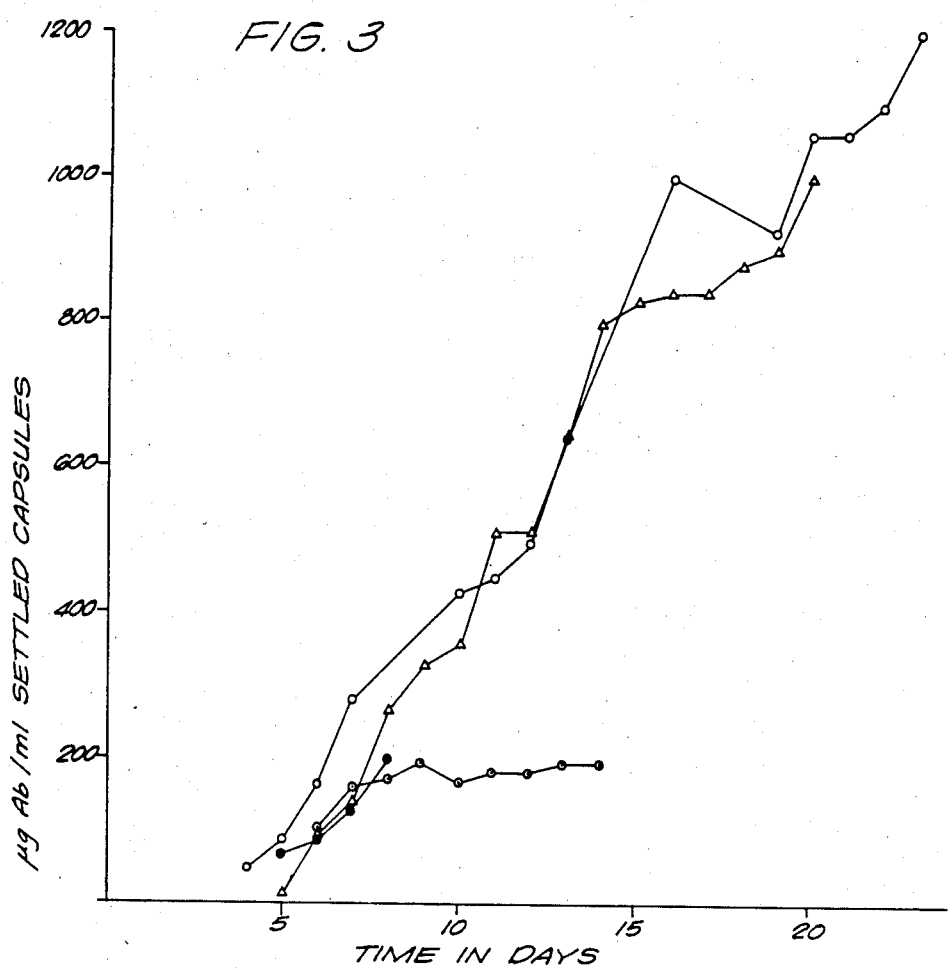
FIG. 3 illustrates antibody production from cultures grown in the media of FIG. 1.

FIG. 3 illustrates the increase in antibody production using the hypertonic medium. At day 14, Culture 397, which was fed isotonic medium on a continuous basis, was producing approximately 200 micrograms of antibody per milliliter of capsules, an excellent antibody yield from a cell culture. In comparison, the cultures grown in the hypertonic medium (390 and 396) were producing approximately 800 micrograms of antibody per milliliter of capsules, a four-fold increase. Antibody concentration was measured by disrupting the capsule membrane and using an ELISA antibody assay. Specifically, a rat-antimouse antibody, coupled to alkaline phosphatase, was reacted with the intracapsular fluid. P-nitrophenyl phosphate was used as a substrate for the alkaline phosphate immunologically coupled to the mouse antibody, and the absorbance of 340 nm was measured.

These experiments show that the increase in antibody content is an effect of the hypertonicity of the medium, not the additional iron. Both Cultures 396 and 397 received the identical media having additional iron except 396 received double the amino acids. There was no lack of amino acids in Culture 397 since it was continually fed isotonic medium with amino acids. As is evident from the data, using a hypertonic medium, in this case 360 milliosmoles, rather than the conventional isotonic medium, one can induce increased protein production without degrading cell viability.

EXAMPLE 2

This example illustrates that, while encapsulation of a cell culture and the addition of an excess of amino acids to make the medium hypertonic greatly increases antibody synthesis, making a medium hypertonic by addition of sodium can yield a small increase in antibody production even for unencapsulated antibody-producing cells.

Three different media were used in this experiment: one having a osmolarity of 250 milliosmoles (hypotonic), a second having a osmolarity of 325 milliosmoles (isotonic), and a third having a osmolarity of 400 milliosmoles (hypertonic). The osmolality of each solution was measured by freezing point depression. Osmolarity of a solution is approximately equal to the osmolality at these concentrations. The media were identical to the base medium set forth in Tables 1 through 3 (without the excess iron or amino acids) except the sodium chloride concentration was varied to change the osmolarity.

Figure 4:
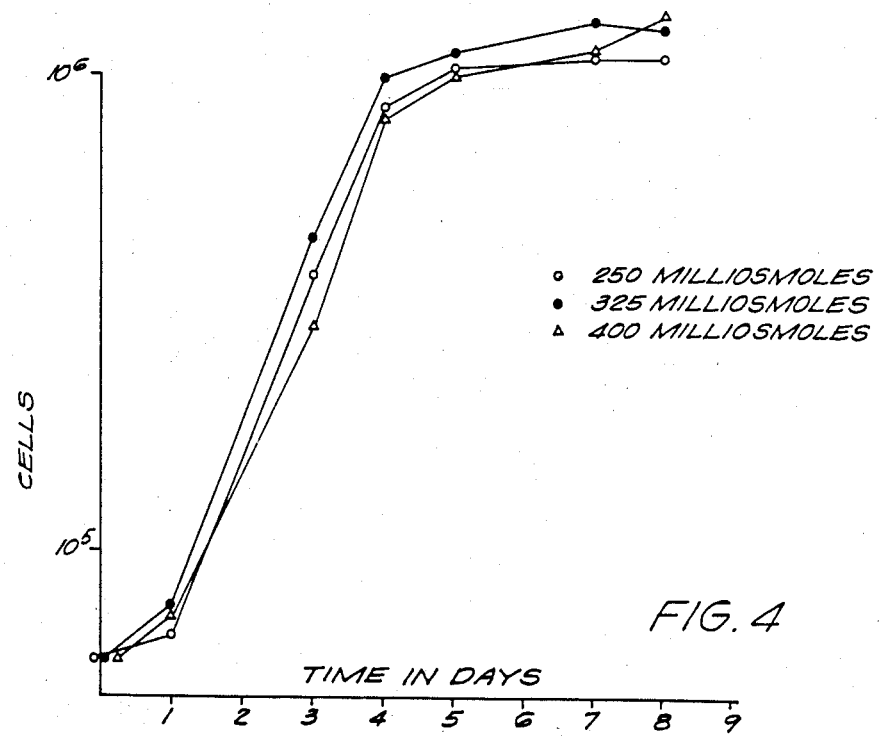
FIG. 4 illustrates that sodium chloride can be used to make the medium hypertonic without loss of cell viability.

FIG. 4 illustrates the cell growth for the three cultures. As is evident from the Figure, changing the osmolarity of the solution by addition of saline had no significant effect on the cell growth.

Table 4 shows the difference in antibody production caused by modification of the solution osmolarity. Three sets of cultures (A–C), each run in duplicate (a,b), are illustrated in Table 4. All of the cultures were the same hybridoma culture but were in unencapsulated form.

TABLE 4

| | Osmolarity | Ab (µg/ml) | Average µg/ml |
| --- | --- | --- | --- |
| A | 250a | 72.9 | 73 |
| | 250b | 74.1 | |
| | 325a | 72.3 | 75 |
| | 325b | 78.8 | |
| | 400a | 79.9 | 78.8 |
| | 400b | 77.7 | |
| B | 280a | 68.2 | 67.1 |
| | 250b | 66.0 | |
| | 325a | 58.6 | 75.1 |
| | 325b | 91.8 | |
| | 400a | 52.4 | 70.6 |
| | 400b | 88.9 | |
| C | 250a | 69.7 | 67.5 |
| | 250b | 65.3 | |
| | 325a | 92.5 | 87.6 |
| | 325b | 82.8 | |
| | 400a | 79.9 | 90.3 |

TABLE 4-continued

| Osmolarity | Ab (µg/ml) | Average µg/ml |
|---|---|---|
| 400b | 100.8 | |

As is illustrated by the data, increasing the osmolarity of the growth medium by the addition of saline results in protein production that is as good as, or better than, the antibody production from the isotonic medium, and better than the hypotonic medium. As is also evident from the data, the effects are not as dramatic as those illustrated in FIG. 3 with media made hypertonic with amino acid addition. Cultures grown in sodium chloride modified hypertonic media thus are characterized by better antibody production than conventional cell cultures. However, the effect of inducing the increase in osmolarity by the addition of amino acids results in a dramatic and unobvious improvement.

Additional experiments have been performed using protein-producing cells such as human-human hybridomas which form IgM as well as other mouse-mouse hybridomas which are IgG producers. In all cases, the hypertonic medium produces greater amounts of protein than the isotonic medium. Media containing additional amino acids having an osmolarity of about 350–360 milliosmoles appear optimum, but other hypertonic media which supply sufficient nutrients also promote antibody and other protein production.

Those skilled in the art may determine other modifications or variations of the procedures and products described herein. Such other modifications and variations are included within the following claims.

What is claimed is:

1. A method of promoting antibody production in antibody-producing cells of mammalian origin comprising the step of culturing a multiplicity of said antibody-producing cells disposed in a plurality of permeable capsule membranes in a medium made hypertonic by the addition of excess amino acids and having an osmolarity in the range of about 340 to 400 milliosmoles.

2. The method of claim 1 wherein said excess amino acids are added continuously to maintain the hypertonicity of said medium.

3. The method of claim 1 wherein the osmotic pressure of said hypertonic medium is between about 340 and 400 milliosmoles.

4. The method of claim 1 wherein said membranes comprise a polymer containing a plurality of primary amine groups salt-bonded to an acidic polysaccharide.

5. The method of claim 4 wherein said acidic polysaccharide comprises alginate.

6. The method of claim 4 wherein said polymer containing a plurality of primary amine groups comprises a polypeptide.

7. The method of claim 1 wherein the osmotic pressure of said hypertonic medium is about 360 milliosmoles.

8. The method of claim 1 wherein said antibody-producing mammalian cell is a genetically modified cell.

9. The method of claim 8 wherein said antibody-producing mammalian cell is a hybridoma.

10. The method of claim 21 wherein said antibody-producing cell is a myeloma.

* * * * *